United States Patent [19]

McKenzie

[11] Patent Number: 5,108,411
[45] Date of Patent: Apr. 28, 1992

[54] FLEXIBLE CATHETER DRIVE CABLE

[75] Inventor: John R. McKenzie, San Francisco, Calif.

[73] Assignee: Cardiovascular Imaging Systems, Inc., Sunnyvale, Calif.

[21] Appl. No.: 500,818

[22] Filed: Mar. 28, 1990

[51] Int. Cl.⁵ .............................................. A61B 17/32
[52] U.S. Cl. ................................... 606/159; 604/264; 606/170
[58] Field of Search ........................ 128/772, 656–658; 604/22, 95, 164, 264; 606/159, 161, 167–171; 57/214, 218

[56] References Cited

U.S. PATENT DOCUMENTS

| | | | |
|---|---|---|---|
| 3,416,531 | 12/1968 | Edwards | 128/660.03 |
| 4,102,118 | 7/1978 | Wheeler | 57/236 |
| 4,215,703 | 8/1980 | Willson | 128/660.03 |
| 4,445,509 | 5/1984 | Auth | 606/159 |
| 4,664,112 | 5/1987 | Kensey et al. | 606/170 X |
| 4,682,607 | 7/1987 | Vaillancourt et al. | 128/660.03 |
| 4,724,846 | 2/1988 | Evans, III | 128/660.03 |
| 4,747,406 | 5/1988 | Nash | 128/660.03 |
| 4,794,931 | 1/1989 | Yock | 128/660.03 |
| 4,857,046 | 8/1989 | Stevens et al. | 604/22 |
| 4,917,085 | 4/1990 | Smith | 606/159 |
| 4,923,462 | 5/1990 | Stevens | 606/159 |
| 4,932,419 | 6/1990 | de Toledo | 128/772 |
| 4,936,845 | 6/1990 | Stevens | 606/159 |
| 4,979,939 | 12/1990 | Shiber | 606/159 |
| 4,990,134 | 2/1991 | Auth | 604/22 |

OTHER PUBLICATIONS

Brochure No. 750-66395 from S.S. White Industrial Products.

Primary Examiner—John D. Yasko
Assistant Examiner—Adam J. Cermak
Attorney, Agent, or Firm—Townsend and Townsend

[57] ABSTRACT

A catheter comprises a flexible tubular member having a drive cable disposed in a lumen thereof. A work element is secured to a distal end of the lumen while a coupling member for rotating the cable secured to the proximal end thereof. The cable includes a more flexible end located within the distal region of the catheter and a less flexible section located within the proximal region of the catheter. In this way, the drive cable is able to transmit torque sufficiently from the proximal end to the distal end even when the catheter is subject to tortuous twisting and bending as a result of positioning within confined regions of the body, such as the vascular system.

23 Claims, 2 Drawing Sheets

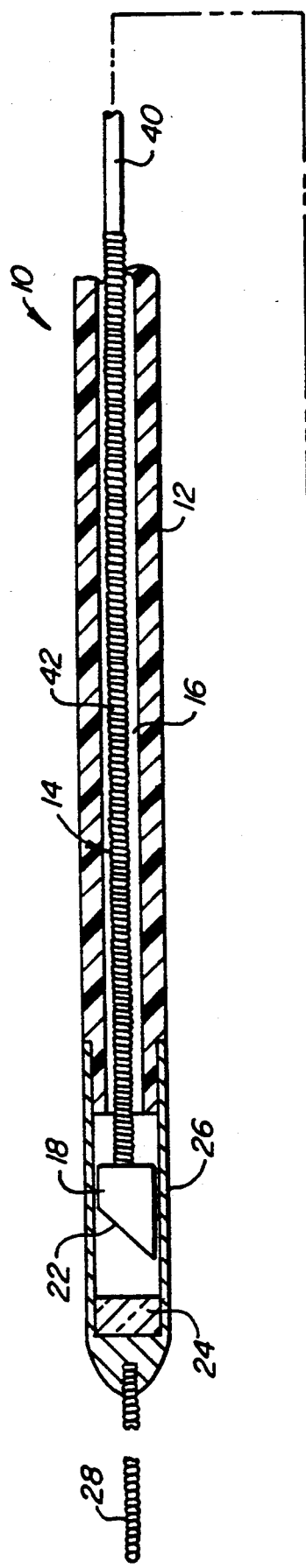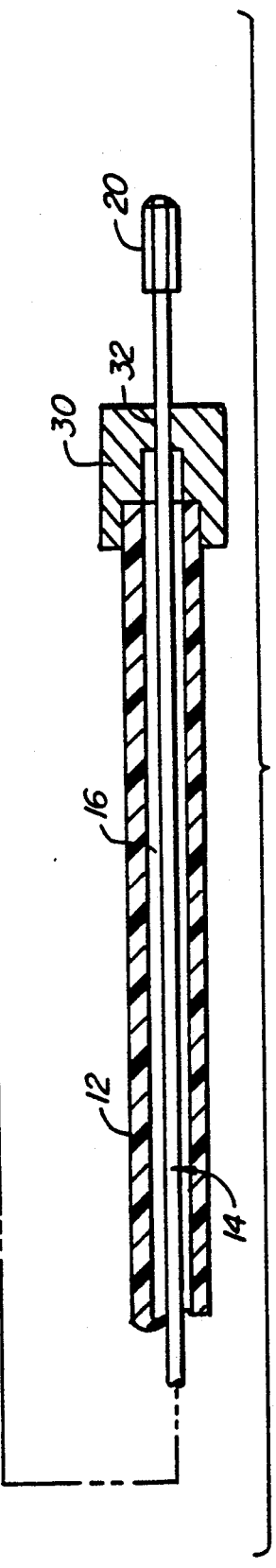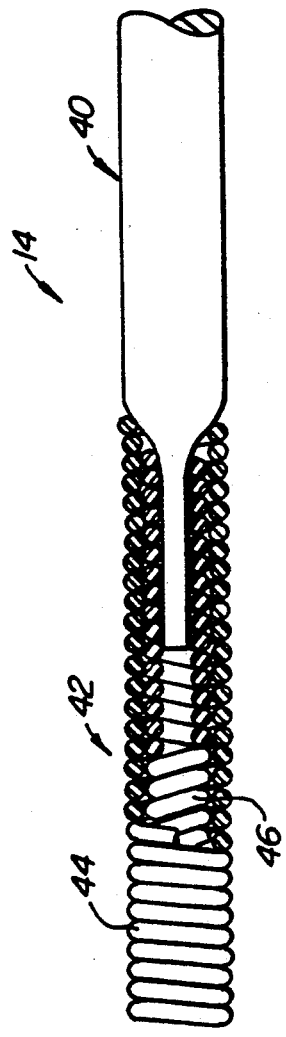
FIG._1.
FIG._2.

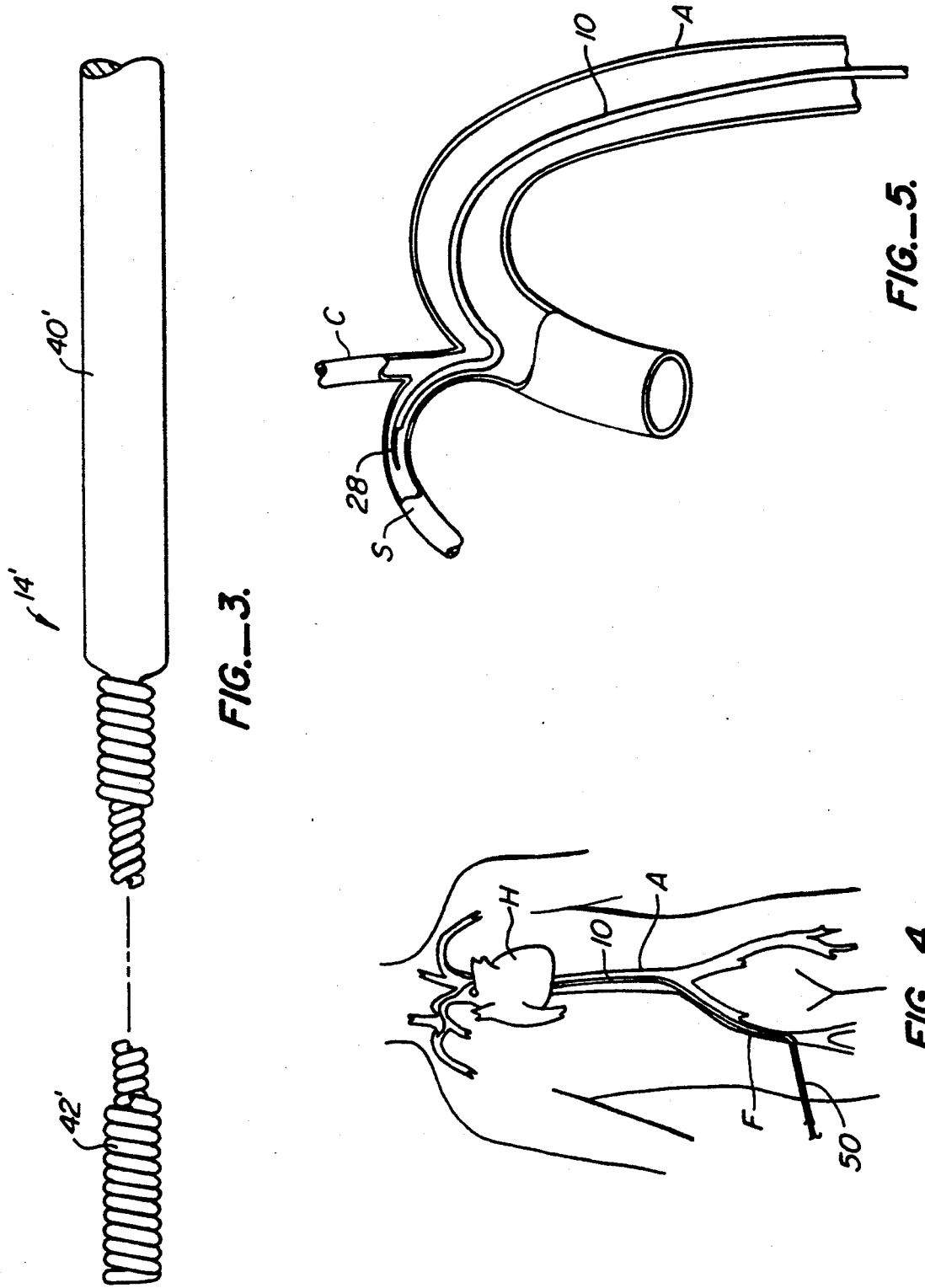

FLEXIBLE CATHETER DRIVE CABLE

BACKGROUND OF THE INVENTION

1. Field of the Invention

The present invention relates generally to the construction of catheters and more particularly to the construction of vascular catheters having internal drive cables for rotating a work element at the distal end of the catheter.

A variety of vascular catheters employ rotatable work elements at their distal ends. For example, vascular imaging catheters may employ a rotating ultrasonic transducer, or fixed transducer in combination with a rotating mirror, in order to scan an imaging beam around the distal end of the catheter. Alternatively, interventional vascular catheters may employ rotating blades, abrasive elements, laser directing elements, and the like. Such catheters frequently utilize a flexible drive cable in order to transmit a rotational drive force from a motor located at the proximal end of the catheter to the work element located in the distal end. In addition to rotation, it is frequently desirable to be able to axially translate the work element within the catheter, preferably by simply pushing or pulling on the proximal end of the drive cable.

The need to transmit rotational motion, i.e., torque, and optionally axial motion places substantial mechanical requirements on the drive cable. The drive cable must possess a certain torsional stiffness in order to adequately deliver rotational force along the relatively long path traversed by the cable. In particular, it is undesirable for the drive cable to experience substantial "wind up" which occurs as a result of twisting along its length. Additionally, it is undesirable for the cable to experience excessive bending which can cause seizing of the cable within the catheter lumen in which it is located. Both of these problems are exacerbated by the tortuous path which the catheter must follow in vascular applications. In particular, the drive cable must be sufficiently flexible to bend around the tight turns presented by the vascular system while maintaining the ability to rotate, frequently at very high rpm, as well as the ability to axially translate through the catheter lumen at all times.

Heretofore, drive cables have usually consisted of solid core wires or braided cables. Such cable constructions, however, have generally represented a compromise between providing the torsional stiffness needed to avoid excessive wind up and flexural stiffness needed to adequately transmit axial force and the flexibility necessary to avoid seizing and binding of the cable within the catheter lumen.

It would therefore be desirable to provide improved drive cables for catheters having cable-driven work elements at their distal end. In particular, it would be desirable to provide drive cables which have sufficient torsional stiffness to avoid excessive wind up, sufficient flexural stiffness to avoid seizing and binding of the cable within the catheter lumen, while remaining sufficiently flexible in order to negotiate the tortuous path which is dictated by passage of the catheter through the vascular system. It would be further desirable to provide drive cables having very narrow diameters, particularly at their distal end, in order to allow construction of small catheters which can enter very small diameter blood vessels. It would be further desirable to provide drive cables which are capable of operating at high rpm while bent across the narrow curvature of the vascular system without experiencing excessive metal fatigue.

2. Description of the Background Art

U.S. Pat. No. 4,794,931, the disclosure of which is incorporated herein by reference, discloses a vascular catheter having a flexible drive cable extending through a central lumen. The cable is disclosed as being formed from stainless steel, with a helically braided wire configuration. Work elements, including ultrasonic transducers, mirrors, and cutting blades, are attached to the forward end of the drive cable. Guide wires having variable flexibility are described in U.S. Pat. Nos. 4,724,846; 4,682,607; 3,416,531; and 4,215,703. U.S. Pat. No. 4,747,406, describes an articulated support tube which facilitates bending a drive cable around tight radii. Nested coil torque cables are commercially available from S.S. White Industrial Products, Inc., Piscataway, N.J., and described in brochure no. 750-66395.

SUMMARY OF THE INVENTION

According to the present invention, a catheter includes a flexible tubular member and a drive cable extending through a lumen in the tubular member. A work element is secured to the distal end of the drive cable while a means for rotating the cable, such as a mechanical coupler which can connect to a drive motor, is secured to the proximal end. The work element can thus be rotated from the proximal end using the drive cable. In the exemplary embodiment, the work element is a mirror which interacts with a fixed ultrasonic transducer to provide an imaging capability. The work element may also be a cutter, an abrasive head, an ultrasonic transducer, or any other device that is advantageously rotated at the distal end of a catheter.

The drive cable includes at least two sections, i.e., a less flexible section over a proximal portion of the cable and a more flexible section over a distal portion of the cable. In the preferred embodiment, the less flexible section is composed of solid core wire and the more flexible section is composed of at least two nested coils which are wrapped in opposite directions. Both the proximal wire section and the distal coil section provide a very high torsional stiffness so that the rotational motion is efficiently transmitted to the work element and the amount of undesired wind up is minimized. The flexural stiffness of the two sections, however, varies considerably. The proximal section possesses a relatively high flexural stiffness which facilitates axially positioning the catheter within the vascular system or elsewhere. In particular, it is possible to push forward on the drive cable, even while rotating at high speeds, to move the catheter forward without significant "bunching" of the cable which can cause seizing and binding. The distal portion of the drive cable, in contrast, has a relatively low flexural stiffness which allows it to accommodate tight curves and small radius bends, such as those found in the vascular system. In this way, a distal portion of the drive cable will be suitable for entering highly tortuous paths while retaining the ability to rotate and transmit rotational energy. The flexible section will further resist metal fatigue which frequently affects the performance of more rigid drive cable elements under similar circumstances.

BRIEF DESCRIPTION OF THE DRAWINGS

FIG. 1 illustrates a vascular catheter constructed in accordance with the principles of the present invention.

FIG. 2 is a detailed view of the drive cable of the catheter of FIG. 1 shown with portions broken away.

FIG. 3 shows an alternate construction of the drive cable of the present invention.

FIG. 4 illustrates the catheter of FIG. 1 introduced to the subclavian artery of a patient.

FIG. 5 illustrates the positioning of the catheter of FIG. 4 in detail.

DESCRIPTION OF THE SPECIFIC EMBODIMENTS

The present invention comprises an improved drive cable for catheters of the type employing a rotating work element at their distal end. The catheter will include a flexible tubular body having at least one lumen which receives the drive cable. The drive cable is connected to the work element at its distal end, and the work element may thus be rotated by turning the drive cable from the proximal end, typically using a motorized drive unit.

The catheter may be intended for a wide variety of medical uses, being particularly suitable for uses which require the distal end of the catheter to be passed through tortuous passages, such as the arteries of the heart. Specific examples of catheters which may be modified to include the drive cable of the present invention comprise gastrointestinal catheters, urinary catheters, intrauterine catheters, intracardiac catheters, and, in particular, intravascular catheters. The catheters of the present invention may be intended for a wide variety of medical procedures, including imaging, cutting, abrading, biopsy, laser ablation, and virtually any other diagnostic or interventional procedure where a rotating work element would find use. The present invention is particularly suitable for ultrasonic catheters used for imaging the interior of blood vessels where the work element is either an ultrasonic transducer or a mirror capable of reflecting ultrasonic energy from a fixed transducer. The construction of medical catheters for a wide variety of such purposes is well described in the medical and patent literature. The construction of an intravascular ultrasonic imaging catheter is described in U.S. Pat. No. 4,794,931, the disclosure of which has previously been incorporated herein by reference.

The drive cable comprises an elongate member, usually a narrow diameter cylindrical member, which rotationally connects a rotating means, such as a mechanical coupler, located at the proximal end of the catheter with the work element located at the distal end of the catheter. The length of the drive cable will be sufficient to extend from beyond the proximal end of the tubular member of the catheter to a location at or near the distal end of the catheter where the work element will be located. For vascular catheters, the length of the drive cable will usually be about the same as that of the catheter, typically being in the range from about 10 to 250 cm, more usually being in the range from about 25 to 150 cm.

According to the present invention, the drive cable will comprise at least two sections, including a less flexible section over a proximal portion of the catheter and a more flexible section over a distal portion of the catheter. Usually, both the less flexible section and the more flexible section will have substantially uniform mechanical properties over their respective lengths, but such uniformity is not necessary. In some cases, it may be desirable to vary one or more mechanical properties over the length of each section in order to achieve a desired purpose. For example, it may be desirable to increase the flexibility (i.e., reduce the flexural modulus of elasticity) in the distal direction or to increase the flexibility in the proximal direction. Normally, there will be only two sections in the drive cable and the less flexible section will be axially connected directly to the more flexible section. Alternatively, there may be one or more sections intermediate the more flexible section and the less flexible section.

In order to efficiently drive the work element, it is necessary that the more flexible distal section and the less flexible proximal section both have relatively high torsional stiffness (i.e., torsional modulus of elasticity) but that the flexural stiffness (flexural modulus of elasticity) of the proximal section be substantially greater than that of the distal section. In this way, both the proximal and distal sections will be able to efficiently transmit torque without substantial wind up and springiness. The distal section of the cable, however, will be much more flexible and be able to bend around tight twists and curves in the catheter lumen caused by placement of the catheter in a tortuous path, e.g., certain portions of the vascular system. The proximal section, in contrast, will remain relatively stiff compared to the distal section. Such flexural stiffness is desirable over most of the length of the torque cable since it will minimize bending of the cable within the lumen reducing the chance for seizing and binding of the cable. Suitable mechanical properties for both the proximal and distal sections of the drive cable are set forth in Table 1.

TABLE 1

| Mechanical Properties of Drive Cable | | | | |
|---|---|---|---|---|
| Section | Length | Diameter | Bending Stiffness Constant (in-lb-in) | Torsional Stiffness Constant (in-lb-in/radian) |
| PROXIMAL | | | | |
| Broad: | 10–200 cm | 0.020–0.15 cm | 5–15 | 2–10 |
| Narrow: | 25–150 cm | 0.035–0.075 cm | 8–13 | 4–7 |
| DISTAL | | | | |
| Broad: | 1–50 cm | 0.015–0.15 cm | 0.05–0.15 | 0.10–0.40 |
| Narrow: | 2–15 cm | 0.025–0.050 cm | 0.08–0.12 | 0.20–0.30 |

As used herein and in the claims, bending stiffness constant ($K_B$) is defined as $K_B = RFd$, where
R = bending radius (in.);
F = deflection force (lb.); and
d = length of cable section (in.).

The bending stiffness constant may be measured using a conventional 3-point compression tester, such as the Instron Tensile Compression Tester. The cable section is placed on a pair of supports spaced apart by a known length (L). A deflection force ($F_d$) is applied to the cable section at a location midway between the supports and the resulting deflection measured. The bending radius (R) can then be determined from the measured deflection. Alternatively, the radius can be determined by graphical analysis. In either case, the bending stiffness constant ($K_B$) can then be calculated using the above formula.

As used herein and in the claims, torsional stiffness constant ($K_T$) is defined as:

$$K_T = \frac{\tau L}{\theta}, \text{ where}$$

$\tau$ = applied torque on drive cable section (in-lb)
L = length of cable section (in); and θ = angle of wind up over length (radians).

The torsional stiffness constant may be measured by attaching a known length (L) of the cable from one section at one end to a goniometer and at the other end to a torque measuring instrument. The goniometer is used to apply a known "wind up" (i.e., number of turns measured in radians) to one end of the cable section while the resulting torque is measured at the other end. The torsional stiffness constant ($K_T$) may then be calculated using the above formula.

Referring now to FIGS. 1 and 2, a catheter 10 constructed in accordance with the principles of the present invention comprises a flexible tubular member 12 having a drive cable 14 disposed in a central lumen 16 extending therethrough. A rotatable work element 18 is secured to the forward or distal end of the drive cable 14 and a coupling member 20 is secured to the proximal end of the drive cable. The work element 18 may thus be rotated by turning the coupler member 20, typically using a motorized drive unit. Such motorized drive units are well known in the art. One suitable motorized drive unit is described in U.S. Pat. No. 4,771,774, the disclosure of which is incorporated herein by reference.

As illustrated, work element 18 is a mirror having a reflective surface 22 which is inclined relative to the axial direction. An ultrasonic transducer 24 is located distally of the mirror 18 and means (not illustrated) will be provided for activating the transducer 24 to produce an ultrasonic signal which may be transversely reflected by surface 22. Transducer 24 will also be capable of receiving back a reflected ultrasonic signal which is useful in imaging the area surrounding the distal end of catheter 10. The construction of such ultrasonic imaging catheters is well known in the art and is typified by U.S. Pat. No. 4,794,931, the disclosure of which has previously been incorporated herein by reference.

The mirror 18 and ultrasonic transducer 24 are enclosed in an acoustically transparent housing 26 which is secured to the distal end of the flexible tubular member 12. For vascular applications, a fixed guide wire 28 will usually be attached to the distal tip of housing 26 to facilitate positioning of the catheter 10 within the vascular system. A proximal cap or housing 30 will be provided to seal the proximal end of flexible tube 12. The cap 30 will include an axial passage 32 which receives the proximal end of drive cable 16. The drive cable 14 will be able to reciprocate axially through passage 32, thus allowing axial positioning of the mirror 18 within housing 26 by pushing or pulling on the coupling member 20. Usually, the capability of such axial positioning of the mirror 18 or other work element will be provided in the motorized drive unit which is utilized.

The drive cable 14 includes a proximal section 40 which comprises a solid wire, typically formed from a stainless steel, such as 304V stainless steel. The wire will have a diameter in the range from about 0.020 to 0.15 cm, more usually being in the range from about 0.035 to 0.075 cm. The length will vary within the limits set forth above depending on the particular application.

Drive cable 14 further comprises a more flexible distal section 42 which includes a pair of nested coils 44 and 46 (FIG. 2). The coils are each formed from metal wire, again typically being a stainless steel such as 304V stainless steel. The inner coil 42 will have a diameter in the range from about 0.01 to 0.125 cm, while the outer coil 44 will have a diameter in the range from about 0.015 to 0.15 cm. The wire diameter of the coils will be in the range from about 0.0025 to 0.020 cm, more usually being in the range from about 0.0050 to 0.010 cm and the coils will have a pitch which may vary from about 8 to 400 turns/cm, more usually being in the range from about 25 to 100 turns/cm. Although only two coils are illustrated, it will be appreciated that additional coils may be added. The coils 44 and 46 are wound in opposite directions so that when the cable 14 is rotated, one of the cables will tend to tighten. Thus, a very high torsional modulus of elasticity may be achieved, while the flexural modulus of elasticity is decreased because of the flexible nature of the coil structures. Optionally, it may be desirable to cover the outer coil 42 in an elastomeric sheath in order to enhance the mechanical integrity of the coil and facilitate rotation within the catheter lumen. Suitable sheath materials include polyurethane and silicone.

The diameter of both the proximal section 40 and the distal section 42 of the drive cable 14 will usually be the same, as illustrated in FIG. 2. In some cases, it may be desirable to provide a proximal section 40' (FIG. 3) having a diameter which is greater than that of the distal section 42', as illustrated in FIG. 3. Such a construction may be advantageous as it provides for enhanced flexural and torsional stiffness in the proximal section 40' in comparison to a wire having a more narrow diameter.

Referring now to FIGS. 4 and 5, placement of the catheter 10 of the present invention into the subclavian artery of the vascular system will be described. Catheter 10 may be introduced to the vascular system through the femoral artery F using an introducing sheath 50, as illustrated in FIG. 4. The catheter 10 is passed up the femoral artery and into the aorta A and then upward past the heart H to the vicinity of the carotid artery C and subclavian artery S (FIG. 5). As can be seen, the region surrounding the juncture of the aorta A, carotid artery C, and subclavian artery S, includes a number of tight curves which cause the catheter 10 to assume a highly contorted configuration. The drive cable 14 within the contorted region of the catheter 10, however, is the flexible distal portion 42 which can rotate within the lumen even across such tight curves. The remaining portion of the catheter 10 which is in the aorta A and femoral artery F, is generally less contorted so that the less flexible section 40 of the drive cable will be adequate.

Although the foregoing invention has been described in detail for purposes of clarity of understanding, it will be obvious that certain modifications may be practiced within the scope of the appended claims.

What is claimed is:

1. A catheter comprising:
   a flexible tubular member having proximal and distal ends and at least one lumen therethrough;
   a drive cable extending through said lumen, said drive cable comprising a less flexible section over a proximal portion thereof and a more flexible section over a distal portion thereof;
   wherein the less flexible section of the drive cable has a flexural stiffness in the range from about 5 to 15 in-lb-in and a torsional stiffness in the range from about 2 to 10 in-lb-in and the more flexible section has a flexural stiffness in the range from about 0.05 to 0.15 in-lb-in and a torsional stiffness in the range from about 0.10 to 0.40 in-lb-in.

2. A catheter as in claim 1, wherein the less flexible section of the drive cable is composed of a solid wire and the more flexible section of the drive cable is composed of nested coils which are wrapped in opposite directions.

3. A catheter as in claim 2, wherein the solid wire is stainless steel having a diameter in the range from about 0.020 to 0.15 cm.

4. A catheter as in claim 2, wherein the nested coils include an inner stainless steel coil having a diameter in the range from about 0.01 to 0.125 cm and an outer stainless steel coil having a diameter in the range from about 0.015 to 0.15 cm.

5. A catheter as in claim 2, wherein the flexible section has a length in the range from about 1 to 50 cm and the proximal section has a length in the range from about 10 to 200 cm.

6. A catheter as in claim 2, wherein the nested coils are covered by an elastomeric sheath.

7. A catheter as in claim 1, wherein the work element is a mirror.

8. A catheter as in claim 1, wherein the work element is an ultrasonic transducer.

9. A catheter as in claim 1, wherein the work element is selected from the group consisting of a cutter and an abrasive head.

10. A drive cable for a catheter, said drive cable comprising a distal section composed of a solid wire and a proximal section composed of nested coils which are wrapped in opposite directions, wherein the distal section has a flexural stiffness in the range from about 5 to 15 in-lb-in and torsional stiffness in the range from about 2 to 10 in-lb-in and the proximal section has a flexural stiffness in the range from about 0.05 to 0.15 in-lb-in and a torsional stiffness in the range from about 0.10 to 0.40 in-lb-in.

11. A drive cable as in claim 10, wherein the solid wire is stainless steel having a diameter in the range from about 0.025 to 0.15 cm.

12. A drive cable as in claim 10, wherein the nested coils include an inner stainless steel coil having a diameter in the range from about 0.01 to 0.125 cm and an outer stainless steel coil having a diameter in the range from about 0.015 to 0.15 cm.

13. A drive cable as in claim 10, wherein the distal section has a length in the range from about 1 to 50 cm and the proximal section has a length in the range from about 10 to 200 cm.

14. A drive cable as in claim 10, wherein the nested coils are covered by an elastomeric sheath.

15. An improved catheter of the type including a flexible tubular member and a drive cable extending axially through the tubular member for rotating a work element secured to the distal end of the cable, said improvement comprising a drive cable having a less flexible section over a proximal portion thereof and a more flexible section over a distal portion thereof, wherein at least a portion of the less flexible section extends into the lumen of the flexible tubular member, wherein the less flexible section of the drive cable has a flexural stiffness in the range from about 5 to 15 in-lb-in and a torsional stiffness in the range from about 2 to 10 in-lb-in and the more flexible section has a flexural stiffness in the range from about 0.05 to 0.15 in-lb-in and a torsional stiffness in the range from about 0.10 to 0.40 n-lb-in.

16. A catheter as in claim 15, wherein the less flexible section of the drive cable is composed of a solid wire and the more flexible section of the drive cable is composed of nested coils which are wrapped in opposite directions.

17. A catheter as in claim 16, wherein the solid wire is stainless steel having a diameter in the range from about 0.025 to 0.15 cm.

18. A catheter as in claim 16, wherein the nested coils include an inner stainless steel coil having a diameter in the range from about 0.01 to 0.125 cm and an outer stainless steel coil having a diameter in the range from about 0.015 to 0.15 cm.

19. A catheter as in claim 15, wherein the flexible section has a length in the range from about 1 to 50 cm and the proximal section has a length in the range from about 10 to 200 cm.

20. A catheter as in claim 15, wherein the nested coils are covered by an elastomeric sheath.

21. A catheter as in claim 15, wherein the work element is a mirror.

22. A catheter as in claim 15, wherein the work element is an ultrasonic transducer.

23. A catheter as in claim 15, wherein the work element is selected from the group consisting of a cutter and an abrasive head.

* * * * *